Figure 1:
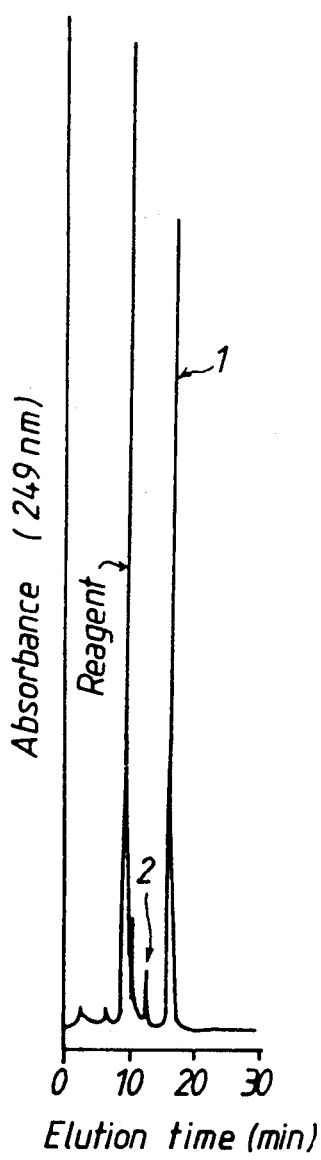

United States Patent [19]

Lee et al.

[11] Patent Number: 5,142,031
[45] Date of Patent: Aug. 25, 1992

[54] METHOD FOR LABELLING SUGARS

[75] Inventors: Yuan C. Lee, Timonium, Md.; Susumu Honda, Kawachinagano; Kazuaki Kakehi, Nara, both of Japan

[73] Assignee: Takara Shuzo Co., Ltd., Kyoto, Japan

[21] Appl. No.: 773,325

[22] Filed: Oct. 11, 1991

[30] Foreign Application Priority Data

Oct. 12, 1990 [JP] Japan .................. 2-272313

[51] Int. Cl.⁵ .................. G01N 33/00; G01N 31/00; C07H 1/00
[52] U.S. Cl. .................. 536/1.1; 435/810; 435/975; 436/8; 436/13; 436/14; 436/15; 436/71; 436/87; 536/4.1; 536/124
[58] Field of Search .................. 536/1.1, 4.1, 124; 435/810, 975; 436/8, 13, 14, 15, 71, 87

[56] References Cited

U.S. PATENT DOCUMENTS

| | | | |
|---|---|---|---|
| 4,391,904 | 7/1983 | Litman et al. | 436/537 |
| 4,659,732 | 4/1987 | Stegelmeier et al. | 514/404 |
| 4,670,460 | 6/1987 | Mardin et al. | 514/404 |
| 4,820,689 | 4/1989 | Ikuzawa et al. | 514/8 |
| 4,837,168 | 6/1989 | de Jaeger et al. | 436/800 |
| 4,921,791 | 5/1990 | Yamasaki et al. | 435/7.8 |
| 5,008,243 | 4/1991 | Ikuzawa et al. | 514/8 |

Primary Examiner—Ronald W. Griffin
Attorney, Agent, or Firm—Armstrong & Kubovcik

[57] ABSTRACT

Disclosed herein is a method of labelling a sugar at its reducing end by using 1-(p-methoxyphenyl)-3-methyl-5-pyrazolone, thereby analyzing said sugar with high sensitivity, and to a kit to be used for sugar labelling by this method.

2 Claims, 3 Drawing Sheets

METHOD FOR LABELLING SUGARS

This invention relates to a method for labelling sugars. More particularly, it relates to a method of labelling a sugar at its reducing end by using a specific compound, thereby analyzing said sugar with high sensitivity, and to a kit to be used for sugar labelling by this method.

Recently attention has been focused on the importance of biochemical roles played by the sugar chain structures of glycoconjugates, and the relationship between sugar chain structure and its functions has been demonstrated in succession. Measurements of NMR and MS spectra are now generally used in determining the sugar chain structure. Because of the extremely high purity required of the samples used for these physicochemical means, there has been a demand for the development of a pre-column labelling method which ensures efficient isolation and high-sensitivity analysis. In addition, the importance of the above pre-column labelling method has been widely recognized as a result of the recent progress in the analysis by high-performance liquid chromatography (hereinafter abbreviated as "HPLC") using a reverse-phase, normal-phase or ion-exchange column.

As examples of the pre-column labelling method, are known the method of fluorescence labelling using 2-aminopyridine (Japanese Patent Kokai No. 10177/1989; hereinafter referred to as "PA method"), and the method of preparing UV absorptive derivatives by the use of 3-methyl-1-phenyl-5-pyrazolone [S. Honda, et al.: Analytical Biochemistry, 180, 351–357 (1989); hereinafter referred to as "PMP method"].

The PA method is employed as a pre-column labelling method ensuring high-sensitivity analysis ($10^{-15}$ mol; fmol level), but its labelling reaction involves the two steps: formation of a Schiff base (at 90° C. for 15 minutes), and its reduction (at 90° C. for one hour).

On the other hand, the PMP method involves only one step of labelling reaction (at 70° C. for two hours), but its detection sensitivity ($10^{-12}$ mol; pmol level) is lower than that of the PA method.

Under the circumstances, this invention is intended to provide a new method for labelling sugars by simpler reaction operations under milder conditions, thereby ensuring high-sensitivity detection, and to provide a kit to be used for this new method.

In brief, this invention relates to a method for labelling a sugar, which comprises bonding 1-(p-methoxyphenyl)-3-methyl-5-pyrazolone (hereinafter abbreviated as "PMPMP") to the sugar at its reducing ends. This invention also relates to a kit to be used for carrying out this new labelling method, which comprises PMPMP.

The sugars herein mean monosaccharides, oligosaccharides, polysaccharides, and glycoconjugates, such as glycoproteins, glycolipids and glucosaminoglucans.

When bonding a labelling agent to a sugar, it is convenient to utilize its free reducing end. Of the sugars described above, monosaccharides, oligosaccharides and polysaccharides contain free reducing end, and therefore require no preliminary treatment.

In the case of glycoconjugates, on the other hand, the reducing ends can be liberated by a known preliminary treatment, such as chemical reactions (e.g., hydrazinolysis and N-acetylation, trifluoroacetolysis, alkaline treatment, and ozonolysis), and enzymatic treatments with endoglycosidase, glycopeptidase or endoglycoceramidase.

PMPMP to be bonded to a sugar at its reducing end is a substance first synthesized by Koike, et al. [Journal of Industrial Chemistry, 57, 56–58 (1954)] having the structure represented by the following formula (I).

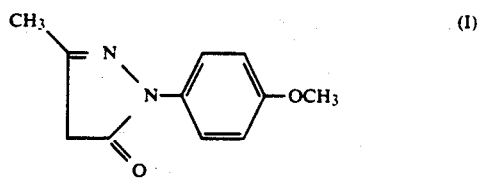

PMPMP used in this invention may be prepared by, for example, the method described in the above literature, or by the method established by the present inventors, in which PMPMP can be obtained in a high yield from 4-methoxyphenylhydrazine hydrochloride, sodium acetate trihydrate and ethyl acetoacetate.

The labelling method of this invention is the reaction of PMPMP with a sugar at its reducing end (hereinafter referred to as "PMPMP method"); reaction of PMPMP with a sugar containing free reducing end under alkaline conditions gives quantitatively the PMPMP-derivative of the sugar, in which two molecules of PMPMP are bonded to one molecule of sugar at its reducing end.

The sugar may be subjected to reaction with PMPMP in the form of a solution in an aqueous solution of sodium hydroxide, potassium hydroxide or sodium carbonate. The reaction should preferably be carried out under a weakly alkaline condition; for example, the sugar is dissolved in a 0.3 M sodium hydroxide solution, PMPMP is added to this alkaline solution, and the reaction is performed at a pH of about 8. PMPMP is used in the form of a solution in a water-soluble, organic solvent, such as methanol, ethanol and acetonitrile; for example, the reaction is carried out by mixing a solution of sugar in 0.3 M sodium hydroxide solution and a solution of PMPMP in methanol in equal volume. In this reaction, it is preferable to use a large excess of PMPMP compared with the sugar; for example, at least 10 μmol of PMPMP is added to 0.5~5 nmol sugar. The reaction should be carried out at a temperature in the range from room temperature to 100° C. for several minutes to two hours, preferably at 70° C. for 20 minutes. This preferred reaction condition is milder and shorter than the reaction conditions for the PA and PMP methods. The PMPMP-sugar thus formed quantitatively by this PMPMP method may be analyzed by, for example, HPLC.

The excessive amount of PMPMP left in the solution obtained by PMPMP reaction can be removed by, for example, extraction with a solvent, such as ethyl acetate, chloroform, benzene and carbon tetrachloride, preferably with water-saturated ethyl acetate. The extraction can be efficiently effected with no decomposition of the PMPMP-sugar, if the pH of the reaction mixture is adjusted to 5. After removal of the excessive amount of PMPMP, the resulting solution is subjected to concentration to dryness under reduced pressure or freeze-drying under reduced pressure, thus giving the dry PMPMP-sugar. The PMPMP-derivative thus obtained is then dissolved in a proper solvent and subjected to analysis by HPLC. For example, the PMPMP-sugar can be detected with high sensitivity by diluting the solution with 15% aqueous solution of acetonitrile, treating the diluted solution with a reverse-phase ODS coulmn, performing elution by the use of a 0.1 M phosphate buffer containing 20% acetonitrile, and measuring the absorbance of the eluate at 249 nm. The solution from which the excessive amount of PMPMP has been removed may also be directly subjected to HPLC.

The PMPMP-sugars prepared by the method of this invention show UV absorption intensity 1.5 times as high as that of the PMP-sugars obtained by the PMP method; use of the PMPMP method is capable of labelling sugars under milder conditions and analyzing sugars with higher sensitivity, compared with the PMP method. In addition, O-link sugars (containing mucintype sugar chain) can also be labelled and analyzed by HPLC, because the labelling reaction is carried out under a weakly alkaline condition.

Sugars contained in a sample being tested can be easily labelled, if the reagents used for the PMPMP reaction are put together as a kit.

The reagents contained in the kit include PMPMP, a solvent for the same and, as required, a reagent or an enzyme to liberate the reducing end of the sugar being analyzed. The kit may also contain standard samples for analysis, for example, PMPMP-derivative of monosaccharides.

These reagents may be contained in the kit in the form of a solution or a freeze-dried product.

Figures 1, 2:
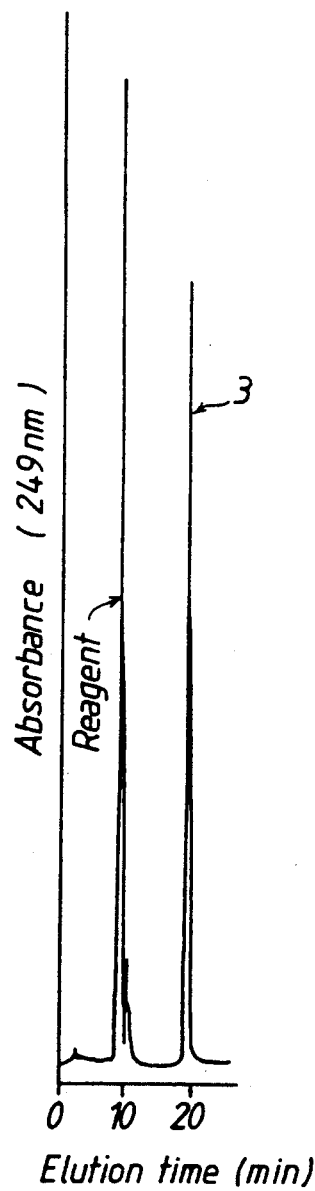
Figure 2:
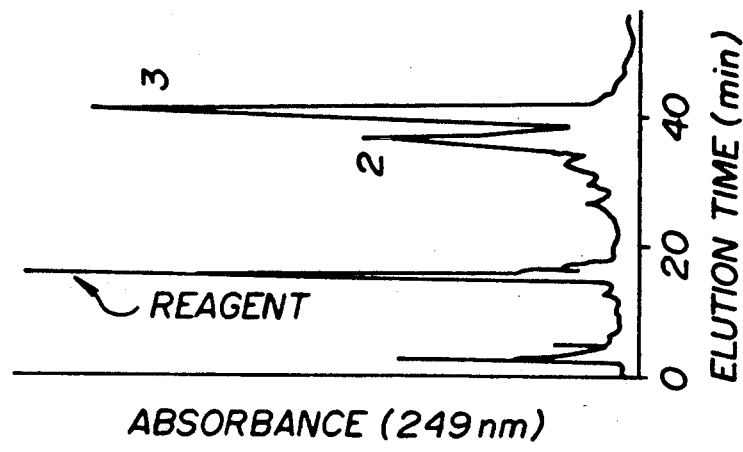
Figures 1, 2:
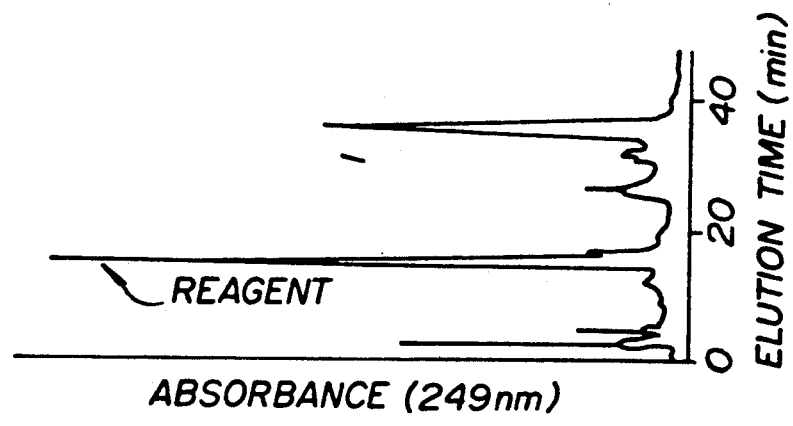
Figure 3:
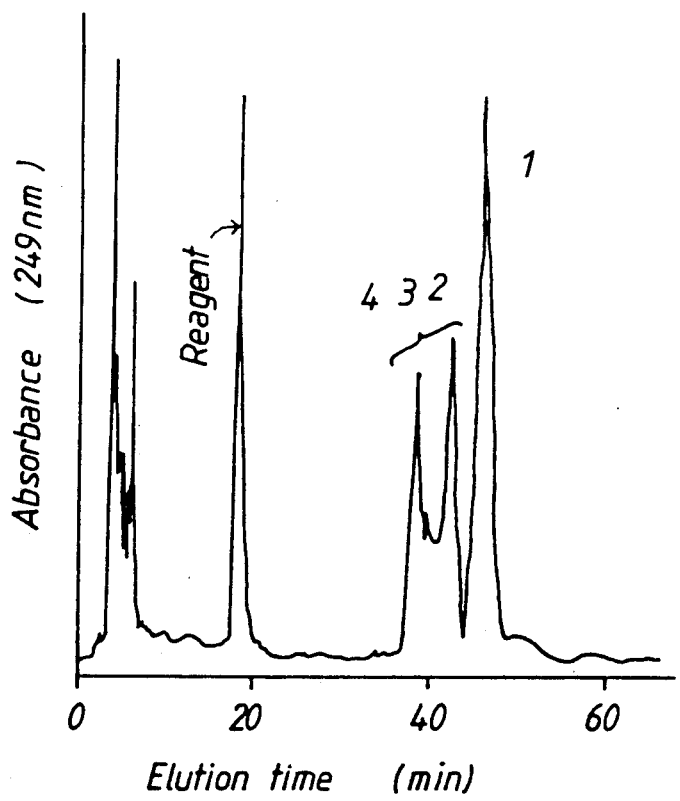

This invention will be explained by the following Examples, and by referring partly to the accompanying drawings, wherein FIG. 1-1, FIG. 1-2, FIG. 2-1, FIG. 2-2 and FIG. 3 show HPLC profiles of the PMPMP-derivative of sialyllactose, of lactose, of disialo-sugar chain, of monosialo-sugar chain and of the sugar derived from ribonuclease, respectively.

REFERENCE EXAMPLE 1

Preparation of PMPMP

4-Methoxy-phenylhydrazine hydrochloride (5.6 g, 32 mmol; product of Aldrich Chem. Co.), sodium acetate trihydrate (5.45 g, 40 mmol; product of Kishida Chemicals) and ethyl acetoacetate (4.16 g, 32 mmol; product of Kishida Chemicals) were dissolved in 40 ml ethanol, and the solution was heated under reflux for two hours to complete the reaction. After cooling, the solvent was distilled off from the reaction mixture under reduced pressure, 40 ml ethanol was added to the residue, and the insoluble matters were removed by filtration. The filtrate was concentrated to dryness under reduced pressure, the residue was dissolved in a small volume of a solvent mixture of benzene and ethyl acetate (4:1), and the solution was subjected to silica gel chromatography (150 g of Silica Gel 60; product of Merck) Elution was performed by using a solvent mixture of benzene and ethyl acetate (4:1), the eluate was concentrated to dryness under reduced pressure, and the residue was recrystallized with methanol, giving 2.80 g (yield: 42.9%) of PMPMP. Its structure was confirmed by $^1$H NMR and $^{13}$C NMR. The spectra thus obtained are shown in Table 1 below.

TABLE 1

$^1$H NMR (500 MHz, CDCl$_3$)
δ: 7.72, 6.90 (4H, H-2', 4', 3', 5'; benzene ring)
3.79 (3H; methoxy group)
3.40 (2H, H-4, 4'; pyrazolone ring)
2.16 (3H; methyl group in pyrazolone ring)
$^{13}$C NMR (125 MHz, CDCl$_3$)
δ: 170.3 (s, C-5)

TABLE 1-continued 157.9, 157.7, 131.3 (3 s, C-1', 4', 3)
123.3, 113.9 (2 d, C-2', 4', 3', 5')
55.4 (q; 4'-methoxy group)
42.9 (t, C-4)
16.8 (q; 3-methyl group)

EXAMPLE 1

(Bonding of PMPMP to Lactose and Sialyllactose)

Sialyllactose (19 μg, 30 nmol; product of Sigma) was weighed into a 1.5-ml polypropylene tube equipped with a screw cap (purchased from Ieda Trading Co.), 20 μl of 0.3 M aqueous solution of sodium hydroxide and 20 μl of 0.5 M methanolic solution of PMPMP were then added thereto, and the tube was capped and held at 70° C. for 20 minutes. At the end of reaction, 20 μl of 0.3 M-HCl was added to adjust the pH of the reaction mixture to 5, extraction with 200 μl of watersaturated ethyl acetate was repeated five times, and the remaining aqueous layer was concentrated to dryness under reduced pressure. The residue was dissolved in 300 μl of 15% aqueous solution of acetonitrile, and 20 μl of the resulting solution was analyzed by HPLC.

Separately, PMPMP was bonded to lactose and the reaction product was analyzed by HPLC in the same manner as above.

HPLC conditions were as listed below.

Column: Capcell pak C$_{18}$ (4.6 mmφ×250 mm; product of Shiseido)
Solvent 0.1 M Phosphate buffer containing 20% acetonitrile (pH: 7.0)
Flow rate: 1.0 ml/min
Detection: 249 nm The results of HPLC for PMPMP-derivatives of sialyl-lactose and of lactose are shown in FIG. 1-1 and FIG. 1-2, respectively. In FIG. 1-1, the ordinate axis shows absorbance at 249 nm, and the abscissa axis shows elution time (minute). Peaks 1 and 2 are both PMPMP-derivatives (α2,3 and α2,6 linkaged) of sialyllactose.

In FIG. 1-2, the ordinate axis and abscissa axis show absorbance at 249 nm and elution time (minute), respectively, and Peak 3 is the PMPMP-derivative of lactose.

As can be seen from these figures, the PMPMP-derivatives of sugars could be isolated absolutely and detected with high sensitivity. In addition, no peak of PMPMP-derivative of lactose is observed in FIG. 1-1, denoting the fact that, in the step of bonding PMPMP to sialyllactose, formation of PMPMP-derivative of lactose caused by elimination of sialic acid residue from sialyllactose did not take place. This indicates that the PMPMP method is a proper method for quantitatively labelling sialo-sugar chain.

EXAMPLE 2

(Bonding of PMPMP to Sugar Chains of Porcine Thyroglobulin)

Disialo-sugar chain fraction and monosialo-sugar chain fraction were prepared from 670 μg (1 nmol) of porcine thyroglobulin by the method of N. Ui, et al. [J. Biochem., 50, 508–518 (1961)], and each of the fractions thus obtained was subjected to hydrazinolysis, N-acetylation and desalting by the use of an ion-exchange resin (Amberlite CG-120) according to the method of B. Bendiak, et al. [Carbohydr. Res., 151, 86–103 (1986)]. The washings were put to the filtrate, the combined solution was concentrated to dryness under reduced pressure, and the residue was treated in the same manner as in Example 1 (bonding of PMPMP, and analysis by HPLC).

HPLC conditions were as listed below.

Column: Capcell pak $C_{18}$ (4.6 mm$\phi$ × 250 mm; product of Shiseido)

Solvent 0.03 M Phosphate buffer containing 15% acetonitrile (pH: 7.0)

Flow rate: 0.6 ml/min

Detection: 249 nm

The results of HPLC for PMPMP-derivatives of disialosugar chain and of monosialo-sugar chain are shown in FIG. 2-1 and FIG. 2-2, respectively. In FIG. 2-1, the ordinate axis shows absorbance at 249 nm, and the abscissa axis shows elution time (minute).

Peak 1 in these figures is the PMPMP-derivative of disialo-sugar chain represented by the following formula (II).

$$S(\alpha 2-6)G(\beta 1-4)GN(\beta 1-2)M(\alpha 1-6) \atop S(\alpha 2-6)G(\beta 1-4)GN(\beta 1-2)M(\alpha 1-3)\Big\rangle \atop {F(\alpha 1-6) \atop | \atop M(\beta 1-4)GN(\beta 1-4)GN-(PMPMP)_2}} \quad (II)$$

(wherein S is sialic acid, G is galactose, GN is N-acetylglucosamine, M is mannose, and F is fucose).

In FIG. 2-2, the ordinate axis shows absorbance at 249 nm, and the abscissa axis shows elution time (minute). Peaks 2 and 3 in the figure are the PMPMP-derivatives of monosialo-sugar chain represented by the following formulas (III) and (IV), respectively, $$G(\beta 1-4)GN(\beta 1-2)M(\alpha 1-6) \atop S(\alpha 2-6)G(\beta 1-4)GN(\beta 1-2)M(\alpha 1-3)\Big\rangle \atop {F(\alpha 1-6) \atop | \atop M(\beta 1-4)GN(\beta 1-4)GN-(PMPMP)_2}} \quad (III)$$

$$S(\alpha 2-6)G(\beta 1-4)GN(\beta 1-2)M(\alpha 1-6) \atop G(\beta 1-4)GN(\beta 1-2)M(\alpha 1-3)\Big\rangle \atop {F(\alpha 1-6) \atop | \atop M(\beta 1-4)GN(\beta 1-4)GN-(PMPMP)_2}} \quad (IV)$$

As can be seen from FIGS. 2-1 and 2-2, efficient labelling of sialo-sugar chains was effected in this Example also.

EXAMPLE 3

(Bonding PMPMP to the Sugar Chains of Ribonuclease B Derived from Bovine Pancreas)

The above-described ribonuclease B (100 μg, 7.1 nmol; product of Sigma Chemical Co.) was subjected to peptidase digestion and gel filtration, thus giving glycopeptide fraction, according to the method of Takahashi, et al. [Biochem. Biophys. Res. Commun., 76, 1194–1201 (1977)]. Glycopeptidase A (Seikagaku Kogyo) was then allowed to act on the fraction obtained above to liberate its sugar chain. The reaction mixture was concentrated to dryness under reduced pressure, PMPMP was bonded to the residue in the same manner as in Example 1, and the product thus formed was analyzed by HPLC in the same manner as in Example 2.

The result of HPLC analysis for the PMPMP-derivative of sugar chains are shown in FIG. 3, in which the ordinate axis shows absorbance at 249 nm, and the abscissa axis shows elution time (minute).

Peak 1 in the figure is the PMPMP-derivative of sugar chain of the following formula (V), and peaks 2 to 4 are the PMPMP-derivative of sugar chain of the following formula (VI). It is clear that these peaks are efficiently separated from one another.

$$\begin{array}{c} M(\alpha 1-6) \\ \phantom{xxx} \searrow M(\alpha 1-6) \\ M(\alpha 1-3) \phantom{xxxxx} \searrow \\ \phantom{xxxxxxxxx} M(\alpha 1-3) \\ M(\beta 1-4)GN(\beta 1-4)GN-(PMPMP)_2 \end{array} \quad (V)$$

$$M(\alpha 1-2)_{1-3}\left\{\begin{array}{c} M(\alpha 1-6) \\ \phantom{xxx} \searrow M(\alpha 1-6) \\ M(\alpha 1-3) \phantom{xxxxx} \searrow \\ \phantom{xxxxxxxxx} M(\alpha 1-3) \\ M(\beta 1-4)GN(\beta 1-4)GN-(PMPMP)_2 \end{array}\right. \quad (VI)$$

EXAMPLE 4

(Preparation of a Kit for Labelling Sugars)

A kit containing PMPMP and methanol (solvent for dissolving PMPMP) was prepared as a reagent for bonding PMPMP to sugars. Its composition is shown in Table 2 below.

TABLE 2

| Agent I | PMPMP | 102 mg | (for 50 tests) |
|---|---|---|---|
| Agent II | Methanol | 1 ml | (for 50 tests) |

REFERENCE EXAMPLE 2

(Comparison of the PMP Method with the PMPMP Method)

PMP and PMPMP were each bonded to glucose, and the products formed were compared with each other.

(1) Preparation of PMP-derivative of glucose

To a solution of 180 mg (1 mmol) glucose in 10 ml of 0.3 M aqueous solution of sodium hydroxide, was added 10 ml of 0.5 M methanolic solution of PMP, and the solution was heated at 70° C. for two hours to complete the reaction. The reaction mixture was neutralized with 1.0 M-HCl, and concentrated to dryness under reduced pressure. The residue was dissolved in 10 ml water, and the solution was extracted twice with a small volume of chloroform to remove the excess PMP. The aqueous layer was then concentrated to dryness under reduced pressure, giving PMP-derivative of glucose.

(2) Preparation of PMPMP-derivative of glucose

To 0.9 mg (5 nmol) glucose were added 20 μl of 0.3 M aqueous solution of sodium hydroxide and 20 μl of 0.5 M methanolic solution of PMPMP, and the mixture was heated at 70° C. for two hours to complete the reaction. The reaction mixture was neutralized with 3.0 M-HCl, and extracted five times with water-saturated ethyl acetate. The aqueous layer was then concentrated to dryness under reduced pressure, giving PMPMP-derivative of glucose.

(3) HPLC analysis of PMP-derivative and PMPMP-derivative of glucose

These two derivatives of glucose were analyzed by HPLC under the same conditions as in Example 1, and the peak areas were compared.

The PMPMP-derivative showed a peak area about 1.5 times as large as that of the PMP-derivative, indicating that the PMPMP method is capable of detection with a sensitivity about 1.5 times as high as the PMP method.

As is detailed above, this invention provides a simple and high-sensitivity method of sugar labelling, and a kit to be used for this method. According to the method of this invention, it is possible to prepare labelled compounds under mild conditions and to effect microanalysis of sialo-sugar chain and the like.

What we claim is:

1. A method for labelling a sugar, which comprises bonding 1-(p-methoxyphenyl)-3-methyl-5-pyrazolone to the sugar at its reducing end.

2. A kit to be used for carrying out the method according to claim 1, which comprises 1-(p-methoxyphenyl)-3-methyl-5-pyrazolone and ancillary component.